United States Patent [19]

Shiraki et al.

[11] Patent Number: 5,141,645
[45] Date of Patent: Aug. 25, 1992

[54] APPARATUS FOR SEPARATION OF BLOOD COMPONENTS

[75] Inventors: Hiroshi Shiraki; Kiyoko Yamamoto, both of Chikushino; Akiko Kitagawa, Mito; Tatsuhiko Kawaoka, Fujinomiya; Yukihiro Oonaka, Fuji, all of Japan

[73] Assignee: Terumo Corporation, Tokyo, Japan

[21] Appl. No.: 710,390

[22] Filed: Jun. 5, 1991

Related U.S. Application Data

[60] Division of Ser. No. 614,698, Nov. 19, 1990, Pat. No. 5,071,570, which is a continuation of Ser. No. 355,837, May 22, 1989, abandoned, which is a continuation of Ser. No. 5,947, Jan. 22, 1987, abandoned.

[30] Foreign Application Priority Data

Jan. 24, 1986 [JP] Japan .................. 61-13549
May 9, 1986 [JP] Japan .................. 61-104861

[51] Int. Cl.⁵ .................................... B01D 21/00
[52] U.S. Cl. ........................... 210/513; 210/206; 210/514; 210/515; 604/408; 604/410
[58] Field of Search .............. 210/513, 514, 515, 206, 210/252; 422/102; 604/408, 410

[56] References Cited

U.S. PATENT DOCUMENTS

| | | | |
|---|---|---|---|
| 3,870,042 | 3/1975 | Viguier | 604/410 |
| 4,222,379 | 9/1980 | Smith | 604/410 |
| 4,223,675 | 9/1980 | Williams | 604/410 |
| 4,810,378 | 3/1989 | Carmen et al. | 210/206 |
| 4,915,847 | 4/1990 | Dillon et al. | 210/515 |
| 4,917,804 | 4/1990 | Franks et al. | 210/515 |
| 4,938,758 | 7/1990 | Al-Sioufi | 604/410 |
| 4,985,153 | 1/1991 | Kuroda et al. | 210/206 |
| 4,997,577 | 3/1991 | Stewart | 210/257.1 |
| 5,026,347 | 6/1991 | Patel | 604/410 |

FOREIGN PATENT DOCUMENTS

WO8300813 3/1983 World Int. Prop. O. .......... 604/410

Primary Examiner—Robert A. Dawson
Assistant Examiner—Sun Uk Kim
Attorney, Agent, or Firm—Cushman, Darby & Cushman

[57] ABSTRACT

A method for the separation of blood into the components and apparatus thereof, characterized by subjecting the blood to strong centrifugation thereby separating said blood into an upper layer (A) of platelet-deficient blood plasma, an intermediate layer (B) of a mixture of platelets and white blood corpuscles, and a lower layer (C) of a red blood corpuscle concentrate, adjusting the hematocrit value of said red blood corpuscle concentrate of (C) to not more than 80% by diluting said red blood corpuscle concentrate with part of said platelet-deficient blood plasma of (A), and subjecting said mixture of (B) to weak centrifugation thereby separating said mixture into a lower layer of white blood corpuscles and an upper layer of a platelet concentrate, and if desired, subjecting the remaining platelet-deficient blood plasma to the treatments of freezing, thawing, and centrifugation thereby separating said platelet-deficient blood plasma into cryoprecipitate and cryoprecipitate-deficient blood plasma, and anaratus therefor.

3 Claims, 8 Drawing Sheets

APPARATUS FOR SEPARATION OF BLOOD COMPONENTS

This is a division of application Ser. No. 07/614,698 filed Nov. 19, 1990 now U.S. Pat. No. 5,071,570 which is a continuation of Ser. No. 07/355,837 filed May 22, 1989 now abandoned which is a continuation of Ser. No. 07/005,947 filed Jan. 22, 1987 now abandoned.

BACKGROUND OF THE INVENTION

1. Field of the Invention

This invention relates to a method for the separation of blood components and an apparatus therefor. More particularly, this invention relates to a method for the efficient separation of blood components such as red blood corpuscles, white blood corpuscles and platelets from whole blood, and an apparatus therefor.

2. Description of Prior Art:

Hemophilia is an inherited disorder of the blood marked by a permanent tendency to hemorrhage due to the lack of the blood coagulating activity of factor VIII or factor IX. The hemophilia caused by the deficiency of factor VIII is called hemophilia A (factor VIII deficiency, classic hemophilia ) and the hemophilia caused by the deficiency of factor IX is called hemophilia B (factor IX deficiency, Christmas disease). Unfortunately, no radical therapy has yet been established for hemophilia. The conventional therapy inevitably resorted to even today consists of supplementing factor VIII to combat hemophilia A or factor IX, hemophilia B, as occasion demands. When a patient with hemophilia has a hemorrhage, the deficient coagulation factor is administered minimum loss of time. When the patent has to undergo a surgical operation or a dental treatment, this supplementation is to be made in advance of the operation or treatment. The factor VIII is unstable and loses in activity during storage. Thus, the supplementation of the factor VIII necessitates use of fresh blood. The factor IX is so stable that the supplementation factor may be effected by use of preserved blood. When the whole blood or the blood plasma is used, ample supply of a coagulation factor is obtained with great difficulty. The intravenous injection of a concentrated preparation such as a cryoprecipitate, Cohn fraction I, or a concentrated factor VIII for the factor VIII or that of a refined prothrombin for the factor IX has found popular acceptance.

In the preparation of factor VIII, the concentrated preparation of factor VIII is obtained by highly concentrating the factor VIII. The recovery of this concentrate is only about 20% because the coagulating activity of the factor VIII is degraded during the course of the concentration. Further since the blood plasma used as the raw material for this preparation is collected from many donors, the possibility of viruses such as those responsible for hepatitis contaminating the preparation is high. In contrast, the cryoprecipitate is prepared by a simple and convenient procedure from the blood plasma collected from a small number of donors and, therefore, the possibility of viruses contaminating the product is low. Moreover, the recovery of the coagulating activity of the factor VIII is high. Since this preparation is obtained by concentration of a limited extent, however, it has a large liquid content and contains fibrinogen and other extraneous proteins in a large proportion. When it is transfused in a large amount, therefore, it has the possibility of increasing the amount of blood plasma for circulation, elevating the concentration of fibrinogen, and inducing secondary reactions such as hemolysis.

Heretofore, separation of a blood sample into red blood corpuscles, white blood corpuscles, platelets, and various other components has been effected by various operations performed with a blood component separation device as illustrated in FIG. 10, for example. In the blood separation device, a blood component transferring tubular member 4 is attached to a blood collecting bag (parent bag) 3 which is provided with a blood introducing tubular member 2 having a vial needle 1 connected to the leading end thereof. The tubular member 4 is connected to a third satellite bag 5 and, at the same time, joined through a first branching tube 6 and a first liquid separating tube 7 to a first satellite bag 8 and also joined through a second branching tube 9 and a second liquid separating tube 10 to a second satellite bag 11.

In the separation of blood into the components thereof by the use of the blood component separation device configuration as described above, when the whole blood collected from the blood vessel such as, for example, the vein into the blood collecting bag 3 is subjected to weak centrifugation, it is separated into a layer of platelet-rich blood plasma (PRP) and a mixed layer of white blood corpuscles (LC) and concentrated red blood corpuscles (CRC). After the upper PRP layer has been transferred to the first satellite bag 8, the blood component transferring tubular member 4 is separated and the mixed layer remaining in the blood collecting bag is used for blood transfusion with the LC left intact therein. The PRP in the first satellite bag 8 is subjected to strong centrifugation so as to transfer the platelet-deficient blood plasma (PRP) in the upper layer to the second satellite bag 11. The platelet concentrate (PC) which remains in the first satellite bag 8 is pelletized and then allowed to float again in the plasma to produce a platelet preparation. The PPP which has been transferred to the second satellite bag 11 is frozen, thawed, and centrifuged to obtain a cryoprecipitate (AHG). This cryoprecipitate is further centrifuged and the cryoprecipitate-deficient blood plasma (CRP) which occurs as a supernatant is transferred to the third satellite bag 5.

In the method described above, however, since the white blood corpuscles are not specifically separated, the white blood corpuscles which are wholly contained in the red blood corpuscles are simultaneously transfused when the red blood corpuscles are to be transfused. If the white blood corpuscles (lymphocytes) happen to contain adult T cell originated hemophilia antibody (ATLA), the transfusion has entailed the possibility of infecting the patient under treatment with the hemophilia. The ATLA has a long latent period and the patient holding this antibody is not conscious and unaware of any symptom unless the disease manifests itself. There has been a possibility that the patient will unconsciously donate his blood and cause the aforementioned trouble of infection.

An object of this invention, therefore, is to provide a novel method for the separation of blood into the components thereof and an apparatus used for working the method.

An another object of this invention is to provide a method for the separation of blood into the component thereof without any fear of ATLA infection and an apparatus used for working the method.

A further object of this invention is to provide a method for the separation of blood into the components thereof, which method is capable of separating the blood into individual components independently of each other in a closed system and an apparatus for working the method.

SUMMARY OF THE INVENTION

The objects described above are accomplished by a method for the separation of blood into the components thereof, characterized by subjecting the blood to strong centrifugation thereby separating the blood into an upper layer of (A) platelet-deficient blood plasma (PPP), an intermediate layer of (B) a mixed solution of platelets (PC) and white blood corpuscles (LC), and a lower layer of (C) a red blood curpuscle concentrate (PRC), adjusting the hematocrit value (Ht) of the red blood corpuscle concentrate of (C) to a level of not more than 80% by diluting the red blood corpuscle concentrate with part of the platelet-deficient blood plasma of (A), and subjecting the mixed solution of (B) to weak centrifugation thereby separating the mixed solution into a lower layer of white blood corpuscles and an upper layer of a platelet concentrate.

The objects described above are further accomplished by a method for the separation of blood into the components thereof, characterized by subjecting the blood to strong centrifugation thereby separating the blood into an upper layer of (A) platelet-deficient blood plasma (PPP), an intermediate layer of (B) a mixed solution of platelets (PC) and white blood corpuscles (LC), and a lower layer of (C), a red blood curpuscle concentrate (PRC), adjusting the hematocrit value (Ht) of the red blood corpuscle concentrate of (C) to a level of not more than 80% by diluting the red blood corpuscle concentrate with part of the platelet-deficient blood plasma of (A), subjecting the mixed solution of (B) to weak centrifugation thereby separating the mixed solution into a lower layer of white blood corpuscles and an upper layer of a platelet concentrate, and subjecting the remaining platelet-deficient blood plasma to the treatments of freezing, thawing, and centrifugation thereby separating the platelet-deficient blood plasma into a cryoprecipitate and a cryoprecipitate-deficient blood plasma.

This invention further concerns a method for the separation of blood into the components thereof, wherein the strong centrifugation is carried out at 1,700 G to 5,500 G for 4 to 10 minutes. This invention also concerns a method for the separation of blood into the components thereof, wherein the weak centrifugation is carried out at 70 G to 600 G for 4 to 10 minutes.

The objects described above are also accomplished by an apparatus for the separation of blood into the components thereof, comprising a blood collecting container connected via a blood introducing tubular member to a blood collecting needle, a platelet-deficient blood plasma container connected via a first blood component flow means to the blood collecting container, a white corpuscle container connected via a second blood component flow means to the blood collecting container and further connected via a third blood component flow means to the platelet-deficient blood plasma container, and a platelet concentrate container connected via a fourth blood component flow means to the white blood corpuscle container.

The aforementioned objects are further accomplished by an apparatus for the separation of blood into the components thereof, comprising a blood collecting container connected via a blood introducing tubular member to a blood collecting needle, a platelet-deficient blood plasma container connected via a first blood component flow means to the blood collecting container, a white corpuscle container connected via a second blood component flow means to the blood collecting container and further connected via a third blood component flow means to the platelet-deficient blood plasma container, a platelet concentrate container connected via a fourth blood component flow means to the white blood corpuscle container, and a cryoprecipitate-deficient blood plasma container connected via the fourth blood component flow means to the platelet-deficient blood plasma container.

This invention further discloses an apparatus for the separation of blood into the components thereof, wherein the fourth blood component conduit it provided with conduit closure means capable of establishing communication.

DESCRIPTION OF PREFERRED EMBODIMENT

Figure 1:
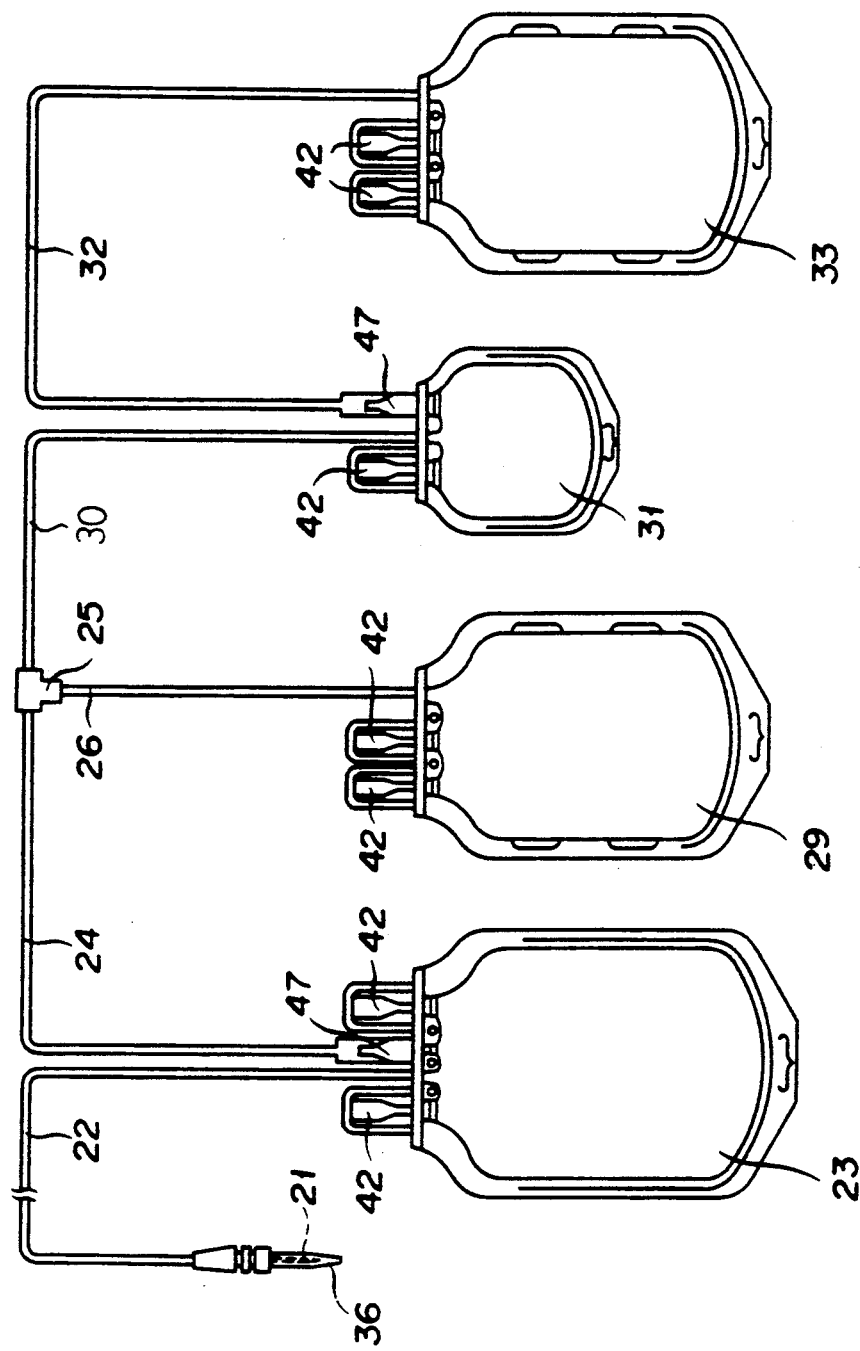
FIGS. 1-7 are front views illustrating typical blood component separation apparatuses embodying the present invention.

Now, the present invention will be described specifically below with reference to the acoompanying drawings. FIG. 1 illustrates a typical blood component separation appratus embodying the present inventon. A blood collecting needle 21 is connected to one end of a blood introducing tubular member (blood collecting tube) 22 and, when necessary, is sheathed with a cap 36. A blood collecting container (blood collecting bag) 23 is connected to the other end of the blood introducing tubular member 22. This blood collecting container 23 is connected to a platelet deficient blood plasma container 29 via first blood component flow means comprising a connecting tube 24, a connector 25, and a connecting tube 26. The blood collecting container 23 is connected to a white blood corpuscle container 31 via second blood component flow means comprising the connecting tube 24, the connector 25, and a connecting tube 30. The white blood corpuscle container 31 is connected to the platelet-deficient blood plasma container 29 via third blood component flow means comprising the connecting tube 30, the connector 25, the connecting tube 26. The white blood corpuscle container 31 is connected to a platelet concentrate container 33 via fourth blood component flow means comprising of a connecting tube 32.

Figure 2:
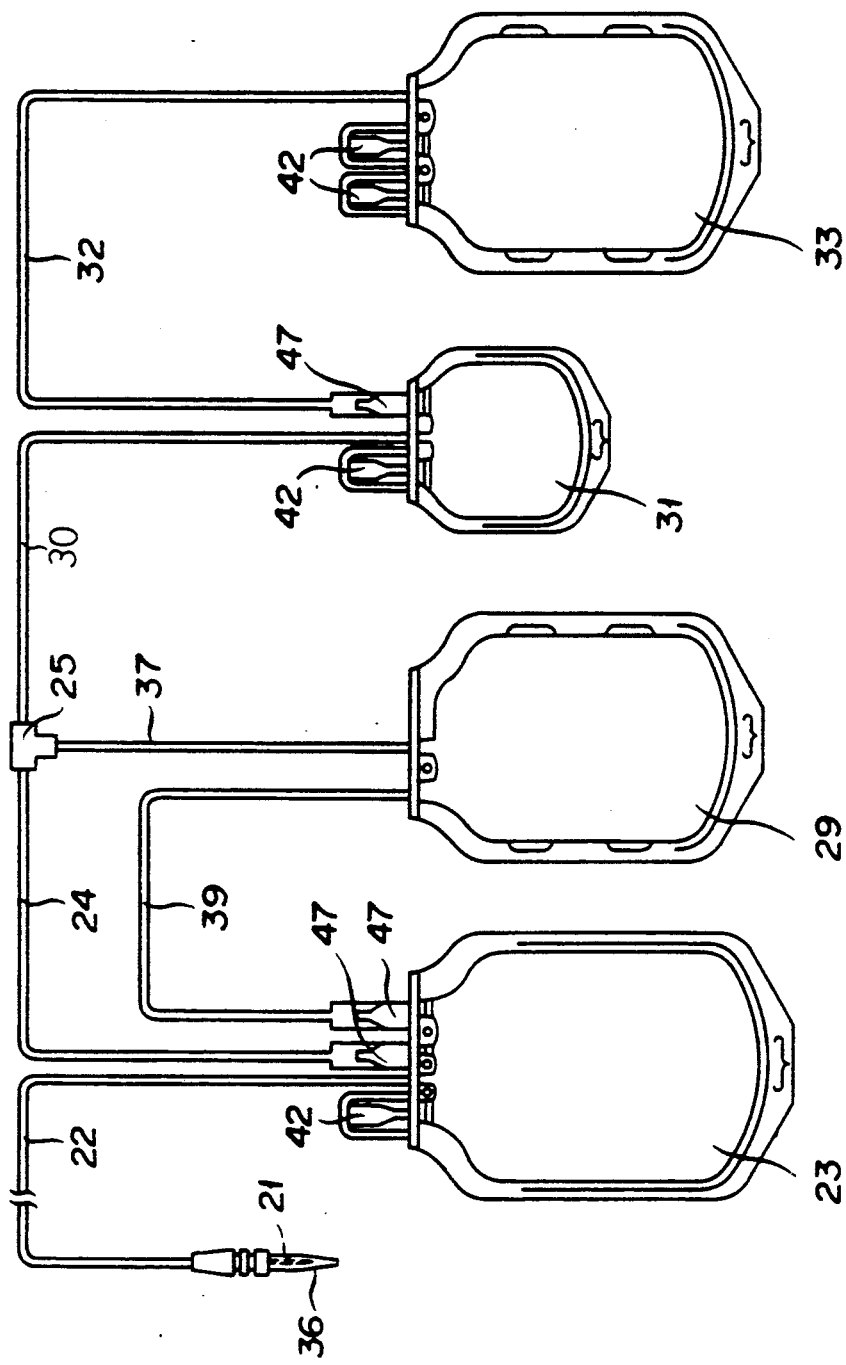

FIG. 2 illustrates another embodiment of this invention. The blood component separation apparatus in this embodiment is identical in configuration with that of the apparatus of FIG. 1, except that a connecting tube 39 for returning the platelet-deficient plasma for diluting the red corpuscle concentrate remained in the blood collecting container 23 is connected from the platelet deficient blood plasma container 29 to the blood collecting container 23.

Figure 3:
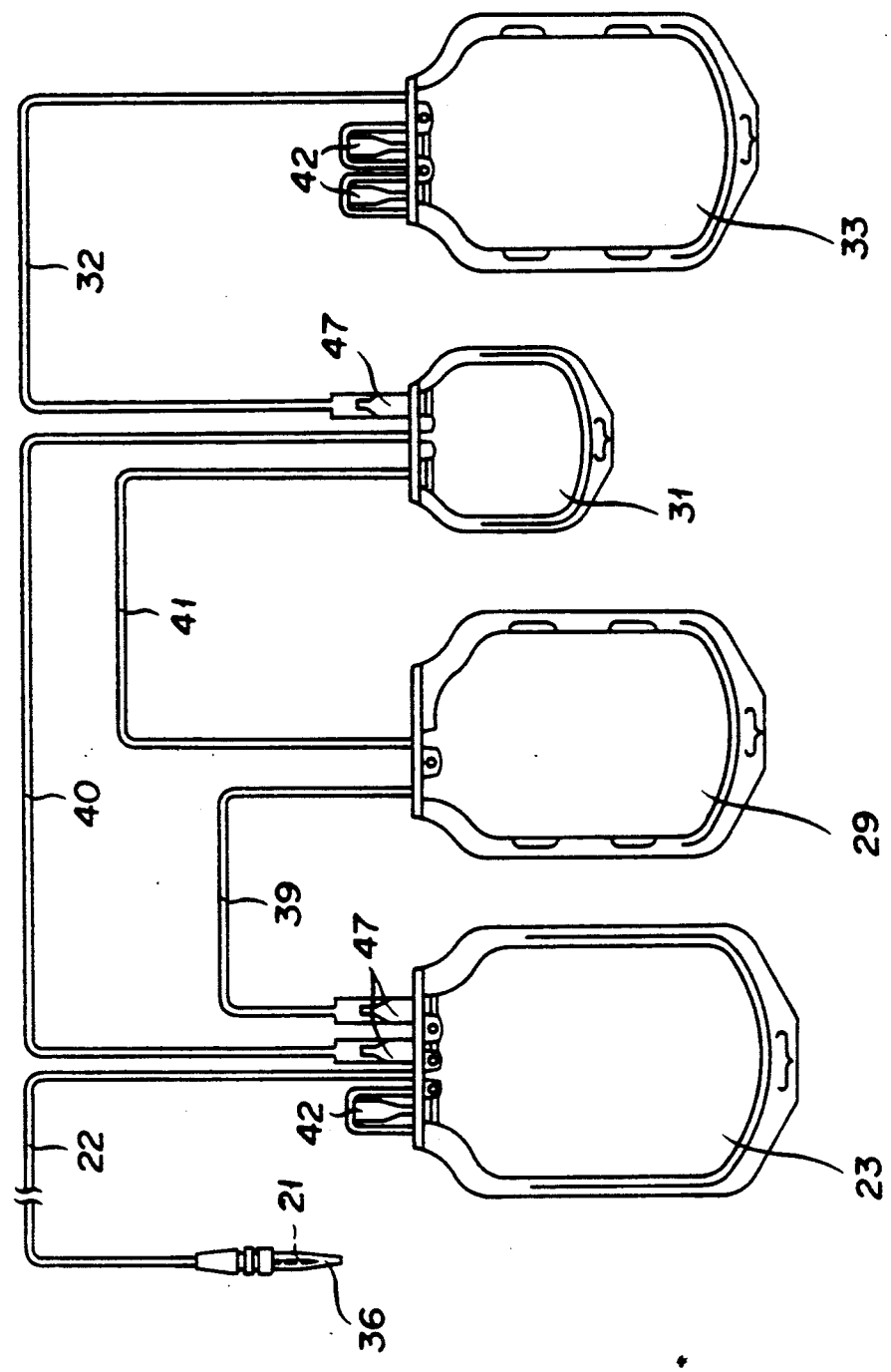

FIG. 3 ilustrates yet another embodiment of this invention. The blood component separation apparatus in this embodiment is identical in configuration with that of FIG. 2, except that the first blood component flow means comprises a connecting tube 39.

Figure 4:
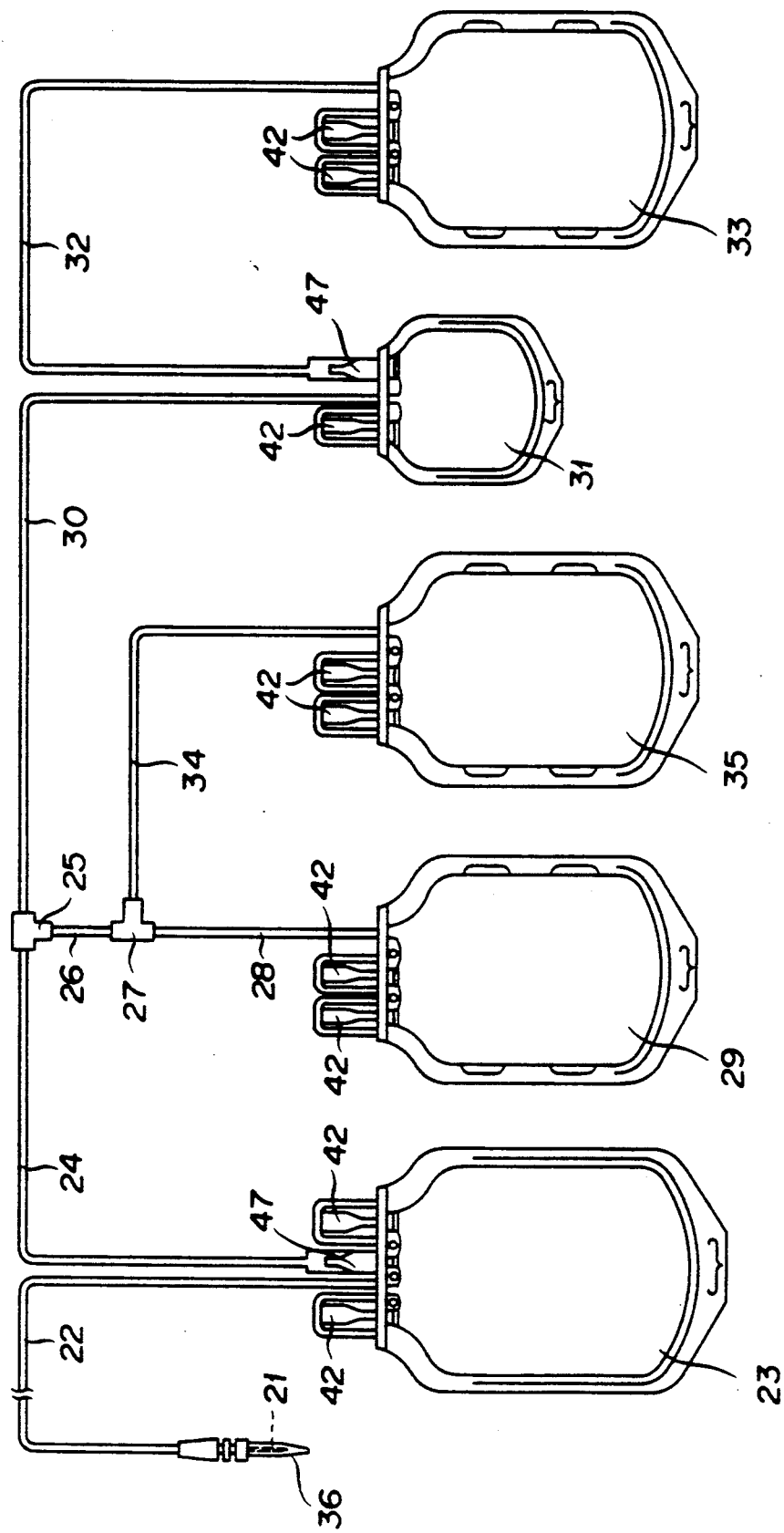

FIG. 4 illustrates still another embodiment of this invention. A blood introducing tubular member (blood collecting tube) 22 has connected to one end thereof a blood collecting needle 21 optionally sheathed with a cap 36 and has connected to the other end thereof a blood collecting container (blood collecting bag) 23. This blood collecting container 23 is connected to a platelet-deficient blood plasma container 29 via a first blood component flow means which comprises a connecting tube 24, a connector 25, a connecting tube 26, and a connecting tube 28. The blood collecting container 23 is connected to a white blood corpuscle container 31 via a second blood component flow means which comprises a connecting tube 24, a connector 25, and a connecting tube 30 and, at the same time, is connected to a platelet-deficient blood plasma container 29 via a third blood component flow means which comprises the connecting tube 30, a connector 25, a connecting tube 26, a connector 27, and a connecting tube 28. The platelet-deficient blood plasma container 29 is connected to a cryoprecipitate-deficient blood plasma container 35 via a fifth blood component flow means comprising a connecting tube 28, a connector 27, and a connecting tube 34. The white blood corpuscle container 31 is connected to a platelet concentrate container 33 via the fourth blood component flow means comprising a connecting tube 32.

Figure 5:
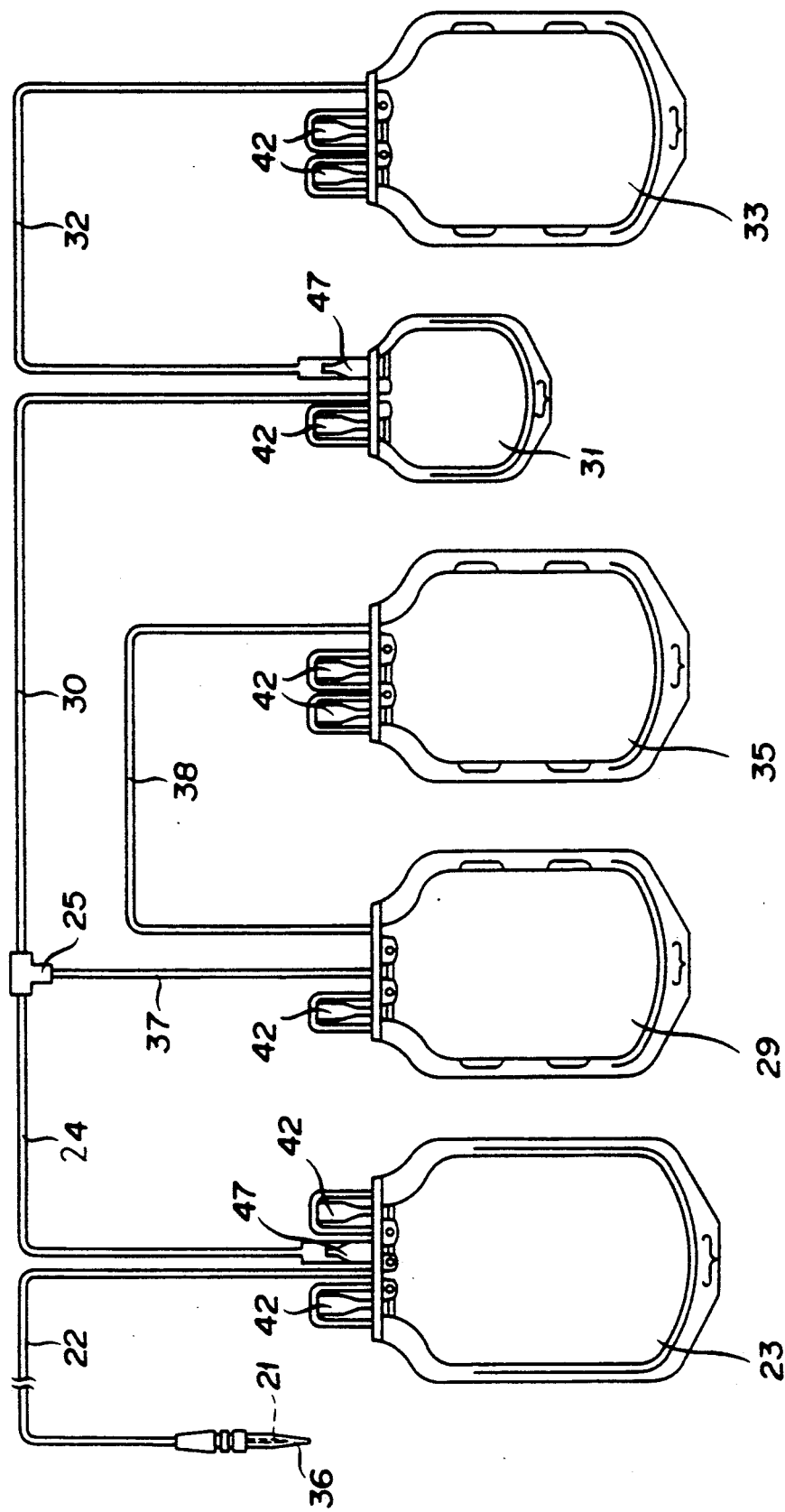

FIG. 5 illustrates a further embodiment of this invention. The blood component separation apparatus in this embodiment is identical in configuration with the apparatus of FIG. 4, except that the fifth blood component flow means is connected to the cryoprecipitate-deficient blood plasma container 35 via the connecting tube 38.

Figure 6:
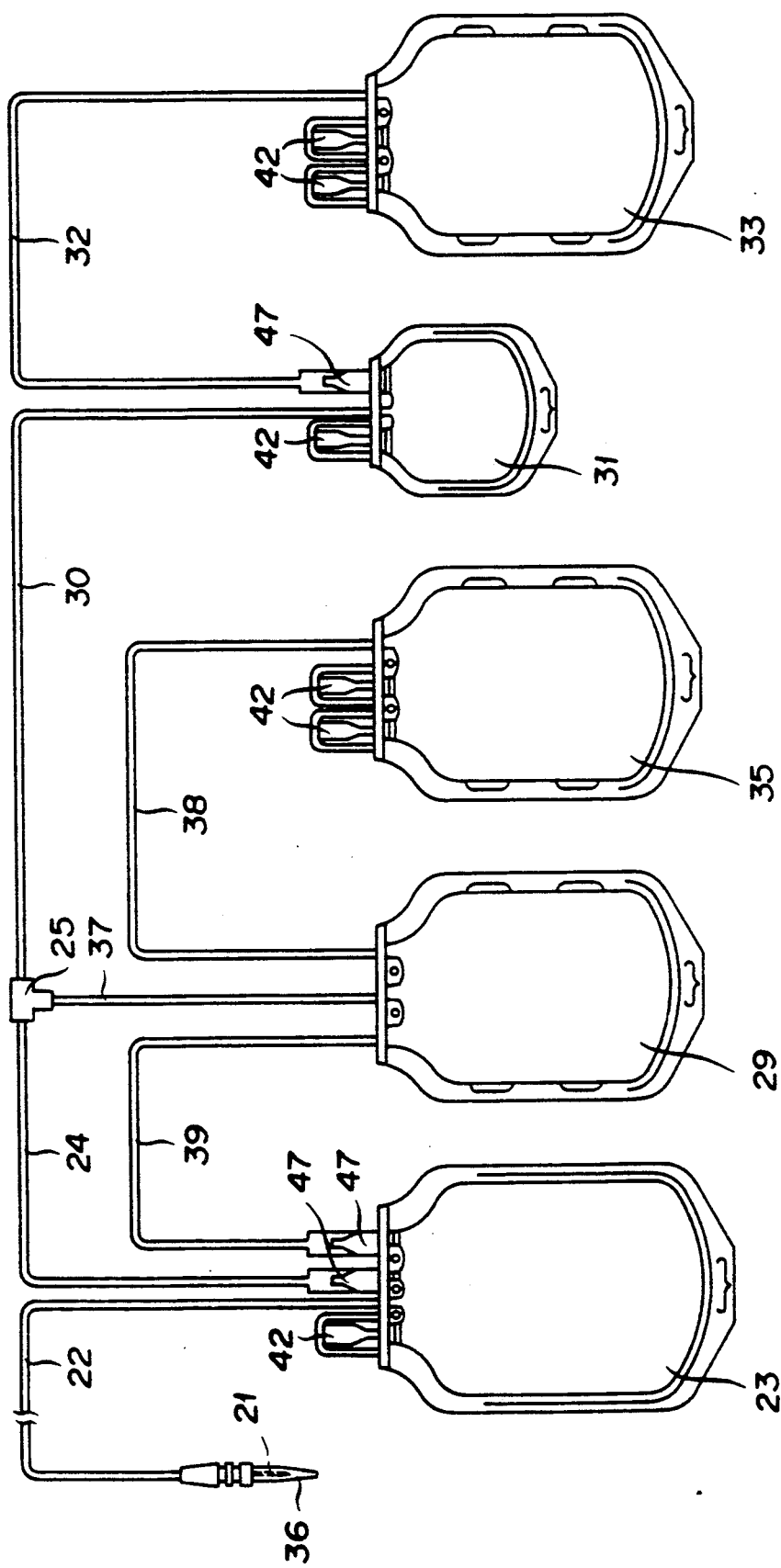

FIG. 6 illustrates still another embodiment of this invention. The blood component separation apparatus in this embodiment is identical in configuration with the apparatus of FIG. 5 except that a connecting tube 39 for returning the platelet-deficient plasma for diluting the red corpuscle concentrate remained in the blood collecting container 23 is connected from the platelet-deficient blood plasma container 29 to the blood collecting container 23.

Figure 7:
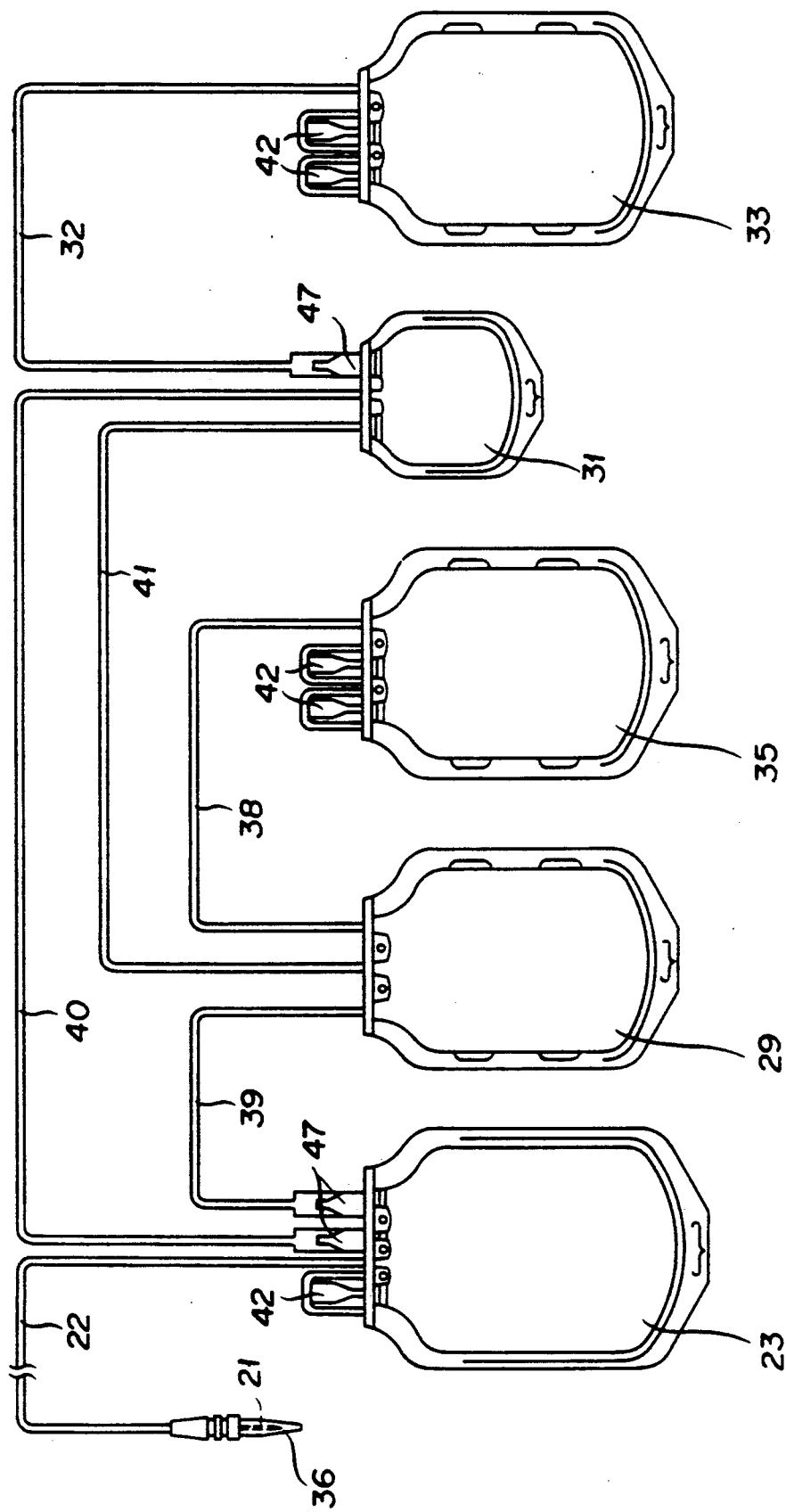

FIG. 7 illustrates a further embodiment of this invention. The blood component separation apparatus in this embodiment is identical in configuration with the apparatus of FIG. 6 excepting the second blood component flow means comprises a connecting tube 40 and the third blood component flow means comprises a connecting tube 41.

In the blood component separation apparatuses described above, all the containers are generally molded of such flexible thermoplastic resins as flexible vinyl chloride resin, and ethylene-vinyl acetate copolymer. These examples are meant as illustrations and not as any limitation. The connecting tubes and the connectors which form the blood component flow means are generally molded of such thermoplastic resin as flexible vinyl chloride resin, ethylene-vinyl acetate copolymer, polycarbonate, and polyethylene terephthalate. These examples are meant as illustrations and not as any limitation. The containers are provided, when necessary, each with a mixed pouring port adapted to be pierced by a vial needle being used for communication with the container interior. This port is covered with a fracturable sealing member 42.

Figure 8:
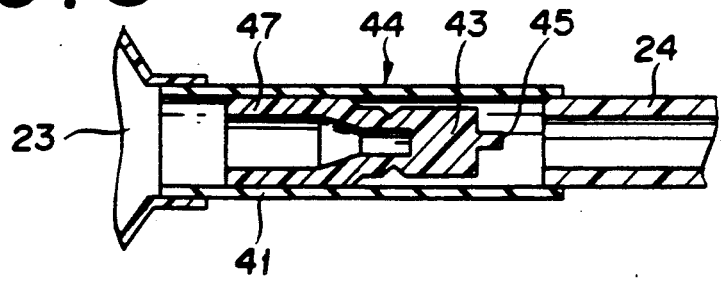
FIG. 8 is a cross section illustrating typical conduit closure means capable of establishing communication.

The connecting tubes are provided, when necessary, each with conduit closure means capable of establishing communication. As the conduit closure means capable of establishing communication, any means which usually keeps the conduit closed and, when required, opens a closure member and permits advance of fluid can be used. One type of the conduit closure means is provided with a fracturable part which is adapted to be fractured so as to permit the conduit to be opened. A typical fracturable part, as illustrated in FIG. 8, comprises a hollow tube 47 having an outside diameter substantially equal to the inside diameter of a liquid passing port and possessing a converged outer end part and a solid columnar member 43 formed integrally with the leading end part of the hollow tube 47 and having an outside diameter smaller than the inside diameter of the liquid passing port and larger than the inside diameter of a tubular member (such as, for example, the member 24), the hollow tube 47 and the solid columnar member 43 both of a rigid synthetic resin such as, for example, rigid vinyl chloride resin and the fractural part attached fast to the inner wall of the liquid passing part 41. A notch 44 is formed near the boundary between the hollow tube 47 and the columnar member 43 on the hollow tube 47 side. Prior to use, the solid columnar member 43 blocks communication between the container (such as, for example, the container 23) and the tubular member (such as, for example, the member 24). Preparatory to use, the solid columnar member 43 is severed across the notch 44 with the external force applied by the finger tip, for example, so as to establish communication between the container and the tubular member. Optionally, the solid columnar member is provided on the end face thereof with a plate projection 45 of a width equal to the outside diameter of the member, so that the solid columnar member 43 fragment severed from the hollow tube 47 will be prevented from clogging the communicating tube.

Figure 9:
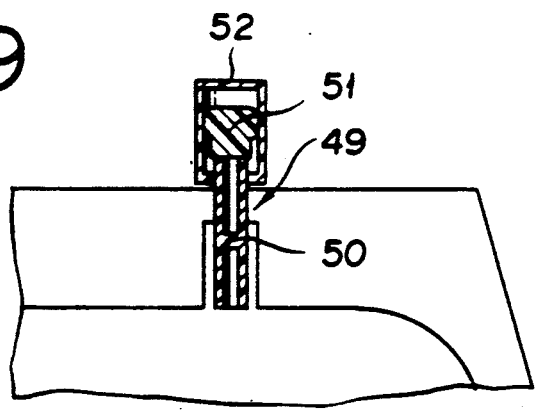
FIG. 9 is a cross section illustrating a typical mixed pouring port.
Figure 10:
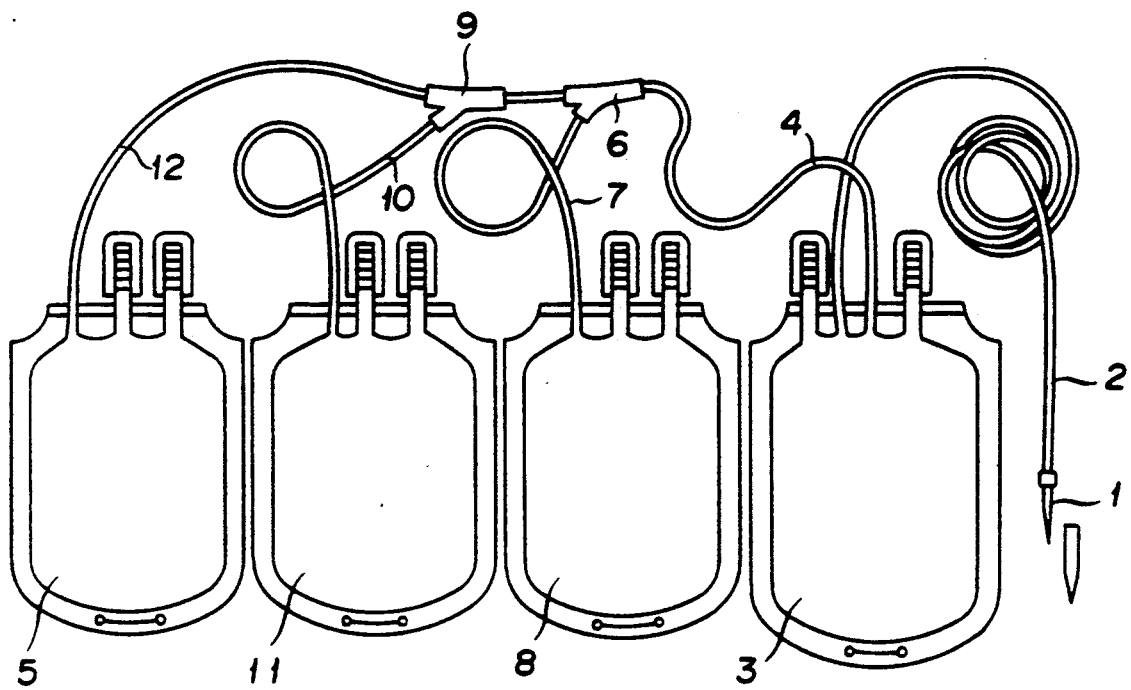
FIG. 10 is a front view illustrating a typical conventional blood component separation apparatus.

The mixed pouring port 49 has the middle part thereof blocked with a diaphragm 50 as illustrated in FIG. 9. It is enabled to permit flow of a fluid as occasion demands by removing a cover 52 capping a rubber member 51 disposed at the leading end of the mixed pouring port 49 and causing a bottle needle to pierce the rubber member 51 and the aforementioned diaphragm 50. When the bottle needle is pulled out, the rubber member 51 will impede backflow. The mixed pouring port 49 may be covered with a fracturable sealing member instead of the cover 52 to permit omission of the aforementioned rubber member 51.

Now, the method for the separation of blood into the components thereof by the use of the apparatus illustrated in FIG. 1 will be described specifically below.

The blood (whole blood) collected in the blood collecting container 23 via the blood collecting needle 21 and the blood collecting tube 22 is set in place as held in the container on a centrifugal separator and subjected to strong centrifugation. This strong centrifugation is carried out at 1,700 G to 5,500 G (G for gravitational acceleration), preferably 2,500 G to 5,500 G, for 4 to 10 minutes. By this strong centrifugation, the blood is separated into an upper layer of platelet-deficient blood plasma (PPP), a first intermediate layer of platelet concentrate (PC), a second intermediate layer of white blood corpuscles (LC), and a lower layer of red blood corpuscle concentrate (PRC). Although the first intermediate layer has a small amount of platelet-deficient blood plasma persisting in the upper part thereof, it is substantially made up of platelets. Although the second intermediate layer at times has a small amount of red blood corpuscles remaining in the lower part thereof, it is substantially made up of white blood corpuscles. By choking the connecting tube 30 with a clamp (not shown) and for the purpose of precluding inclusion of the intermediate layers and securing the blood plasma in the platelet concentrate, the platelet concentrate, with a small amount of the platelet-deficient blood plasma in the upper layer left behind, is separated into the platelet-deficient blood plasma container 29 via the first blood component flow means comprising the connecting tube 23, the connector 25, the connecting tube 26, and the connecting tube 28. Separately, by choking the connecting tube 26 with a clamp (not shown) and loosening the clamp (not shown) on the connecting tube 30, the components of the first and second intermediate layers in combination with the small amount of the platelet-deficient blood plasma and a small amount of red blood corpuscles are separated as a mixture in the white blood corpuscle container 31 via the second blood component flow means comprising the connecting tube 24, the connector 25, and the connecting tube 30. The red blood corpuscles in the lower layer are left behind in the blood collecting container 23.

Then, with the connecting tube 30 choked with a clamp, part of the platelet-deficient blood plasma inside the platelet-deficient blood plasma container 29 is returned via the first blood component flow means to the blood collecting container 23 so as to dilute the red blood corpuscle concentrate to a hematocrit value (Ht value) not exceeding 80%, preferably falling in the range of 50 to 80%, and permit use of blood plasma as a nutrient source for red blood corpuscles. Consequently, there is obtained a red blood corpuscle preparation relieved of not less than about 60% of white blood corpuscles, inclusively of not less than about 80% of lymphocytes.

Separately, the blood collecting container 23 and the platelet-deficient blood plasma container 29 are severed from each other in the connecting tube 26 and the blood collecting container 23 is severed from the white blood corpuscle container 31 and the platelet concentrate container 33 in the connecting tube 30.

The white blood corpuscle container 31 and the platelet concentrate container 33 are subjected to weak centrifugation. This weak centrifugation is carried out at 70 G to 600 G for 4 to 10 minutes. When the platelet concentrate is separated in an upper layer and white blood corpuscles are separated in a lower layer in consequence of this weak centrifugation, the upper layer is transferred into the platelet concentrate container 33. Since this white blood carpuscle container 31 is provided with the conduit closure means 47 capable of establishing communication, the possibility that during and after the separation, any liquid will be accidentally moved into the platelet concentrate container 33 is nil. After the two containers 31 and 33 have been severed from each other, the platelet concentrate in the container 33 is used as a platelet preparation.

Now, the method for the separation of blood into the components thereof by the use of the apparatus illustrated in FIG. 4 will be described specifically below.

The blood (whole blood) collected in the blood collecting container 23 via the blood collecting needle 21 and the blood collecting tube 22 is set in place as held in the container on a centrifugal separator and subjected to strong centrifugation. This strong centrifugation is carried out at 1,700 G to 5,500 G (G for gravitational acceleration), preferably 2,500 G to 5,500 G, for 4 to 10 minutes. By this strong centrifugation, the blood is separated into an upper layer of a platelet-deficient blood plasma (PPP), a first intermediate layer of a platelet concentrate (PC), a second intermediate layer of white blood corpuscles (LC), and a lower layer of a red blood corpuscle concentrate (PRC). The first intermediate layer is substantially made up of platelets, although this layer has a small amount of platelet-deficient blood plasma remaining in the upper part thereof The second intermediate layer is substantially made up of white blood corpuscles, although the layer has a samll amount of red blood corpuscles remaining in the lower part thereof. By choking the connecting tubes 30 and 34 each with a clamp (not shown) and for the purpose of precluding inclusion of the intermediate layers and securing the blood plasma of the platelet concentrate, the platelet concentrate is separated, with a small amount of the platelet-deficient blood plasma left behind in the upper layer, into the platelet-deficient blood plasma container via the first blood component flow means comprising the connecting tube 24, the connector 25, the connecting tube 26, the connector 27, and the connecting tube 28. By choking the connecting tube 26 with a clamp (not shown) and opening the clamp (not shown) on the connecting tube 30, the components of the first and second intermediate layers in combination with the small amount of platelet-deficient blood plasma and small amount of red blood corpuscles are separated as a mixture in the white blood corpuscle container 31 via the second blood component flow means comprising the connecting tube 24, the connector 25, and the connecting tube 30. The red blood corpuscle concentrate in the lower layer is left behind in the blood collecting container 23.

Then, with the connecting tube 30 choked with a clamp, part of the platelet-deficient blood plasma inside the platelet-deficient blood plasma container 29 is returned via the first blood component flow means to the blood collecting container 23 so as to dilute the red blood corpuscle concentrate to a hematocrit value (Ht value) not exceeding 80%, preferably falling in the range of 50 to 80%, and permit use of blood plasma as a nutrient source for red blood corpouscles. Consequently, there is obtained a red blood corpuscle preparation relieved of not less than about 60% of white blood corpuscles, inclusively of not less than about 80% of lymphocytes.

The blood collecting container 23 is severed from the platelet-deficient blood plasma container 29 and the cryoprecipitate-deficient blood plasma container 35 in the connecting tube 26 and the blood collecting container 23 is severed from the white blood corpuscle container 31 and the platelet concentrate container 33 in the connecting tube 30.

The platelet-deficient blood plasma container 29 and the cryoprecipitate-deficient blood plasma container 33 are frozen (at a tmeperature in the range of $-20°$ to $-80°$ C., preferably $-40°$ to $-80°$ C., for example), then thawed, and subjected to centrifugation at 2,500 G to 5,500 G for 15 to 20 minutes to be separated into two layers. The cryoprecipitate-deficient blood plasma in the upper layer is transferred into the cryoprecipitate-deficient blood plasma container 35 and the cryoprecipitate is left behind in the platelet-deficient blood plasma container 29. By severing the two containers 29 and 35 in the connecting tube 28 or 34, the cryoprecipitate in the container 29 is used as the raw mateiral for an antihemophilic preparation.

The white blood corpuscle container 31 and the platelet concentrate container 33 are subjected to weak centrifugation. This weak centrifugation is carried out at 70 G to 600 G for 4 to 10 minutes. This weak centrifugation results in separation of an upper layer of platelet concentrate and a lower layer of white blood corpuscles. The upper layer is transferred to the platelet concentrate container 33. Since this white blood corpuscle container 31 is provided with the conduit closure means 47 capable of establishing communication, the possibility of a liquid accidentally flowing into the platelet concentrate container during or after the separation is nil. After the two containers 31 and 33 have been severed from each other, the platelet concentrate in the container 33 is used for the manufacture of a platelet preparation.

In the method described above, there is involved an operation of returning the platelet-deficient blood plasma in the platelet-deficient blood plasma container 29 to the blood collecting container and using this blood plasma as a nutrient source for red blood corpuscles. Since this operation results in a proportional decrease in the amount of the platelet-deficient blood plasma, it may be desirable to have a red blood corpuscle preserving liquid stored in advance in the cryoprecipitate-deficient blood plasma container 35, subject the liquid to strong centrifugation, and after separation of the blood into the components thereof, transfer the liquid to the blood collecting container 23 and mix it with the contents thereof. In this case, the cryoprecipitate-deficient blood plasma container 35 is desired to be provided with a conduit closure means 47 capable of establishing communication.

A typical example of the red blood corpuscle preserving liquid is a physiological saline solution which contains glucose, adenine, and a colloidal osmoregulatory agent (mannitol).

The method for the separation of blood into the components thereof has been described with respect to the apparatuses illustrate in FIGS. 1 through 4. With the apparatuese illustrate in FIGS. 5 through 7, the separation of blood into the components thereof can be effected by the same procedure as described above.

Now, this invention will be described more specifically below with reference to working examples.

EXAMPLE 1

A blood component separation apparatus configurated as illustrated in FIG. 1 was produced with flexible vinyl chloride resin. In this apparatus, when a blood collecting container 23 having an inner volume of 400 ml and holding 56 ml of CPD liquid in advance therein was charged with 400 ml of human blood (whole blood) and then subjected to strong centrifugation at 3,500 G for 5 minutes, this blood was separated into a layer of platelet-deficient blood plasma, a layer of platelet concentrate, a layer of white blood corpuscles, and a layer of red blood corpuscle concentrate in the descending order. Then, the greater part (about 200 ml) of the platelet-deficient blood plasma, with the small remainder thereof left behind to preclude inclusion of the second and subsequent layers into the platelet-deficient blood plasma, was transferred via first blood component flow means to a platelet-deficient blood plasma container 29 having an inner volume of 300 ml. Further, the platelet concentrate and the white blood corpuscles of the second and third layers and part of the red blood corpuscle concentrate of the fourth layer (about 80 ml) were transferred via the second blood component flow means to a white blood corpuscle container 31 having an inner volume of 80 ml. As the result, about 180 ml of the red blood corpuscle concentrate remained in the blood collecting container 23.

The hematocrit value of this red blood corpuscle concentrate was adjusted to below 80% by adding about 30 ml of the platelet-deficient blood plasma in the platelet-deficient blood plasma container 29 to the red blood corpuscle concentrate. Then the platelet-deficient blood plasma container 29 was svered from the blood corpuscle container 31 and the platelet concentrate container 33 were severed from the blood collecting container 23 and were subjected to weak centrifugation at about 170 G for 5 minutes, with the result that there ensued separation into an upper layer of a platelet concentrate and a lower layer of white blood corpuscles. The upper layer was transferred into the platelet concentrate container 35.

The proportions of white blood corpuscles, red blood corpuscles, and platelets in the various component of blood separated as described above were as shown in Table 1.

In a control, the whole blood was first centrifuged at 1,100 g for about 5 minutes to be separated into a red blood corpuscle concentrate and a platelet-rich blood plasma and then the platelet-rich blood plasma was centrifuged at 3,500 G for about 5 minutes to be separated into a platelet concentrate and blood plasma in accordancce with the conventional method. In the table, the paired values represent the results of his invetnion vs those of the control.

TABLE 1

|  | Red blood corpuscle concentrate | Platelet concentrate |
| --- | --- | --- |
| White blood corpuscles (%) | 41/96 | <½ |
| Lymphocytes (%) | 15/95 | <½ |
| Red blood corpuscles (%) | 96/100 | <1/1 |
| Platelets (%) | 26/34 | 41/63 |

EXAMPLE 2

A blood component separation apparatus configurated as illustrated in FIG. 4 was produced with flexible vinyl chloride resin. In this apparatus, when a blood collecting container 23 having an inner volume of 400 ml and holding 56 ml of CPD liquid in advance therein was charged with 400 ml of human blood (whole blood) and then subjected to strong centrifugation at 3,500 G for 5 minutes, this blood was separated into a layer of platelet-deficient blood plasma, a layer of a platelet concentrate, a layer of white blood corpuscles, and a layer of a red blood corpuscle concenate in a descending order. Then the greater part (about 200 ml) of the platelet-deficient blood plasma, with the small remainder thereof left behind to preclude inclusion of the second and subsequent layers into the platelet-deficient blood plasma, was transferred via a first blood component flow means to a platelet-deficient blood plasma container 29 having an inner volume of 300 ml. Further, the platelet concentrate and the white blood corpuscles of the second and third layers and part of the red blood corpuscle concentrate of the fourth layer (about 80 ml) were transferred via second blood component flow means to a white blood corpuscle container 31 having an inner volume of 80 ml. As the result, about 180 ml of the red blood corpuscle concentrate remained in the blood collecting container 23.

The hematocrit value of this red blood corpuscle concentrate was adjusted to below 80% by adding about 30 ml of the platelet-deficient blood plasma in the platelet-deficient blood plasma container 29 to the red blood corpuscle concentrate. Then, the platelet-deficient blood plasma container 29 and the cryoprecipitate-deficient blood plasma container 35 were severed from the blood collecting container 23 and their contents were frozen at $-60°$ C., thawed, and subjected to centrifugation at about 2,500 G for about 20 minutes, with the result that there ensued separation of an upper layer of cryoprecipitate-deficient blood plasma and a lower layer of cryoprecipitate. When the upper layer was transferred to the cryoprecipitate-deficient blood plasma container 35, there was obtained about 190 ml of cryoprecipitate. About 10 ml of cryoprecipitate remained in the platelet-deficient blood plasma container 29. Separately, the white blood corpuscle container 31 and the platelet concentrate container 33 were severed from the blood collecting container 23 and subjected to weak centrifugation at about 170 G for 5 minutes, with the result that there ensued separation of an upper layer of a platelet concentrate and a lower layer on white blood corpuscles. The upper layer was transferred to the platelet concentrate container 33.

The proportions of white blood corpuscles, red blood corpuscles, and platelets in the various components of blood separated as described above were as shown in Table 2.

In a control, the whole blood was first centrifuged at 1,100 G for about 5 minutes to be separated into a red blood concentrate and platelet-rich blood plasma was centrifuged at 3,500 G for about 5 minutes to be separated into a platelet concentrate and blood plasma in accordance with the conventional method of separation. In the table, the paired values represent the results of this invention vs those of the control.

TABLE 2

|  | Red blood corpuscle concentrate | Platelet concentrate |
|---|---|---|
| White blood corpuscles (%) | 41/96 | <½ |
| Lymphocytes (%) | 15/95 | <½ |
| Red blood corpuscles (%) | 96/100 | <1/1 |
| Platelets (%) | 26/34 | 41/36 |

EXAMPLE 3

In the same apparatus as used in Example 2, the procedure of Example 2 was repeated, excepting the cryoprecipitate-deficient blood plasma container 33 holding therein in advance as a red blood preserving liquid 80 ml of a physiological saline solution containing glucose, adenine, and a colloidal osmoregulatory agent (mannitol) were similarly processed and subjected to strong centrifugation and 80 ml of the physiological saline solution was transferred into the blood collecting container to dilute the red blood corpuscle concentrate.

The results obtained herein were identical with those of Example 2.

As described above, this invention is directed to a method for the separation of blood into the components thereof, characterized by subjecting the blood to strong centrifugation thereby separating the blood into an upper layer (A) of platelet-deficient blood plasma, an intermediate layer (B) of a mixture of platelets and white blood corpuscles, and a lower layer (C) of a red blood corpuscle concentrate, adjusting the hematocrit value of the red blood corpuscle concentrate to not more than 80% by diluting the red blood corpuscle concentrate of (C) with part of the platelet-deficient blood plasma of (A), and subjecting the mixed solution of (B) to weak centrifugation thereby separating the mixed solution into a lower layer of white blood corpuscles and an upper layer of a platelet concentrate. Thus, the strong centrifugation separates the blood into a layer of platelet-deficient blood plasma, a layer of platelets, a layer of white blood corpuscles, and a layer of a red blood corpuscle concentrate in the descending order. Owing to the cushioning property of the layer of white blood ocrpuscles, the platelets are not exposed to the impact of the strong centrifugation and, therefore, are not suffered to aggregate. Further, since the platelets can float in the blood plasma contained in the same container, they can be easily separated from white blood corpuscles by weak centrifugation.

Thus, the method of this invention has no use for the action of agitation which has been indispensable to the conventional method. It also permits ready manufacture of a preparation using platelets of an unimpaired activity. Moreoever, since the platelets are not required to be pelletized as in the conventional method, the damage to the platelets is slight and the platelets permit stable manufacture of a preparation even after overnight's standing following the collection of blood. The period of safe preservation, therefore, can be elongated. Since the red blood corpuscle concentrate denuded of white blood corpuscles by the strong centrifugation contains white blood corpuscles, particualrly lymphocytes, in a very small amount, there is the possibility of the ATLA infection being precluded.

This invention is further directed to a method for the separation of blood into the components thereof, characterized by subjecting the blood to strong centrifugation thereby separating the blood into an upper layer (A) of platelet-deficient blood plasma, an intermediate layer (B) of a mixture of platelets and white blood corpuscles, and a lower layer (C) of a red blood corpuscle concentrate, adjusting the hematocrit value of the red blood corpuscle concentrate of (C) by diluting the red blood corpuscle concentrate with part of the platelet-deficient blood plasma of (A), subjecting the mixture of (B) to weak centrifugation thereby separating the mixtue into a lower layer of white blood corpuscles and an upper layer of a platelet concentrate, and subjecting the remaining platelet-deficient blood plasma to the treatments of freezing, thawing, and centrifugation thereby separating the platelet-deficient blood plasma into a cryoprecipitate and cryoprecipitate-deficient blood plasma. Thus, in addition to the aforementioned effects, this method is capable of obtaining the VIII factor with an extremely high recovery ratio. This VIII factor has the advantage that it is obtained in the form of a highly concentrated preparation and, therefore, does not entail any notable side reaction.

Further, this invention is directed to an apparatus for the separation of blood into the components thereof, comprising a blood collecting container connected via a blood is introducing tubular member to a blood collecting needle, a platelet-deficient blood plasma container connected via a first blood component flow means to the blood collecting container, a white blood corpuscle container connected via a second blood component flow means to the blood collecting container and also connected via a third blood component flow means to the platelet-deficient blood plasma container, and a platelet concentrate container connected via a fourth blood component flow means to the white blood corpuscle container. Thus, this apparatus not only effects separation of blood into the components thereof in a closed system but also permits manufacture of red blood corpuscle concentrate without inclusion of white blood corpuscles and consequent ATLA infection. Since this apparatus has no use for agitation or pelletization, it inflicts minimal injury upon the platelets and permits manufacture of a platelet preparation possessed of stable activity.

This invention is also directed to an apparatus for the separation of blood into the components thereof, comprising a blood collecting container connected via a blood introducing tubular member to a blood collecting needle, a platelet-deficient blood plasma container connected via a first blood component flow means to the blood collecting container, a white blood corpuscle container connected via a second blood component flow means to the blood collecting container and also connected via a third blood component flow means to the platelet-deficient blood plasma container, a platelet concentrate container connected via a fourth blood component flow means to the white blood corpuscle container and a platelet concentrate container connected via a fifth blood component flow means to the platelet-deficient blood plasma container. In addition to the aforementioned affects, therefore, the apparatus has the advantage that the VIII polymerization initiator in a high concentration at a high recovery ratio.

What is claimed is:

1. An apparatus for the separation of blood into the components thereof, comprising a blood collecting container connected via a blood introducing tubular member to a blood collecting needle, a platelet-deficient blood plasma container connected via a first blood component flow means to said blood collecting container, a white blood corpuscle container connected via a second blood component flow means to said blood collecting container and further connected via a third blood component flow means to said platelet-deficient blood plasma container, a platelet concentrate container connected via a fourth blood component flow means to said white blood corpuscle container, and a cryoprecipitatedeficient blood plasma container connected via a fifth blood component flow means to said platelet-deficient blood plasma container.

2. An apparatus according to claim 1, wherein said fourth blood component flow means is provided with conduit closure means capable of establishing communication.

3. An apparatus according to claim 1, wherein said cryoprecipitate-deficient blood plasma container includes a red blood corpuscle preserving liquid therein.

* * * * *